United States Patent [19]
Lowen

[11] Patent Number: 5,041,556
[45] Date of Patent: Aug. 20, 1991

[54] PROCESS FOR THE PREPARATION OF INSECTICIDAL, ACARICIDAL AND MOLLUSCICIDAL 2-HALOPYRROLE-3-CARBONITRILE COMPOUNDS

[75] Inventor: Gregory T. Lowen, Durham, N.C.

[73] Assignee: American Cyanamid Company, Stamford, Conn.

[21] Appl. No.: 625,739

[22] Filed: Dec. 11, 1990

[51] Int. Cl.$^5$ .......................................... C07D 207/30
[52] U.S. Cl. ...................................... 548/560; 548/561
[58] Field of Search ................................ 548/560, 561

Primary Examiner—Robert W. Ramsuer
Assistant Examiner—Joseph K. McKane
Attorney, Agent, or Firm—Alice C. Brennan

[57] ABSTRACT

There is provided a process for the preparation of 2-halopyrrole-3-carbonitrile compounds which are useful as insecticidal, acaricidal and molluscicidal agents.

4 Claims, No Drawings

PROCESS FOR THE PREPARATION OF INSECTICIDAL, ACARICIDAL AND MOLLUSCICIDAL 2-HALOPYRROLE-3-CARBONITRILE COMPOUNDS

BACKGROUND OF THE INVENTION

Pyrrole carbonitrile compounds useful as insecticides, acaricides and molluscicides are described in copending patent application Ser. No. 430,601 filed on Nov. 6, 1989. These compounds may be prepared by halogenating pyrrole-3-carbonitrile.

Pyrrole-3-carbonitrile is difficult to synthesize. Literature methods such as that reported by A. M. van Leusen et al., Tetrahedron Letters, 5337, (1972) report yields of 10% or less.

M. S. Morales-Rios et al., Tetrahedron, 45, pages 6439-6448 (1989) disclose the preparation of methyl 2-chloropyrrole-3-carboxylate from methyl 2-cyano-4,4-dimethoxybutyrate and hydrochloric acid. However, methyl 2-chloropyrrole-3-carboxylate is distinct from the 2-halopyrrole-3-carbonitrile compounds prepared by the process of the present invention.

It is therefore an object of the present invention to provide a new and efficient process for preparing 2-halopyrrole-3-carbonitrile compounds.

SUMMARY OF THE INVENTION

The present invention is directed to a process for preparing insecticidal, acaricidal and molluscicidal 2-halopyrrole-3-carbonitrile compounds of formula I

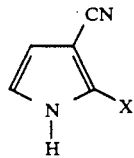

(I)

wherein X is Cl or Br.

Surprisingly, it has been found that in compounds of formula I may be prepared by reacting malononitrile with a base and a haloacetaldehyde di($C_1$-$C_4$ alkyl) acetal of formula II

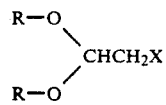

(II)

wherein R is $C_1$-$C_4$ alkyl and X is as described above in the presence of a solvent to obtain a (formylmethyl)-malononitrile di($C_1$-$C_4$ alkyl) acetal compound of formula III

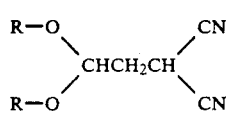

(III)

wherein R is as described above and reacting said formula III compound with a hydrogen halide acid.

DETAILED DESCRIPTION OF THE INVENTION

One of the preferred embodiments of the present invention involves reacting malononitrile with at least 1 molar equivalent, preferably about 1 to 3 molar equivalents, of a base and at least 1 molar equivalent, preferably about 1 to 3 molar equivalents, of a formula II haloacetaldehyde di($C_1$-$C_4$ alkyl) acetal compound as described above in the presence of a solvent preferably at a temperature range of about 0° C. to 100° C. to form a formula III (formylmethyl)malononitrile di($C_1$-$C_4$ alkyl) acetal compound as described above and reacting the formula III compound with at least 1 molar equivalent of a hydrogen halide acid preferably hydrochloric acid or hydrobromic acid at a temperature range of about 15° C. to 100° C. to form 2-halopyrrole-3-carbonitrile compounds of formula I.

The formula I compounds may be isolated by conventional techniques such as dilution of the reaction mixture with water and filtration or, alternatively, extraction with a suitable solvent. Suitable extraction solvents include water-immiscible solvents such as ether, ethyl acetate, toluene, methylene chloride and the like.

Bases suitable for use in the process of the present invention include alkali metal $C_1$-$C_6$ alkoxides, alkali metal hydroxides, alkali metal hydrides, alkali metal carbonates, $C_1$-$C_4$ trialkylamines and pyridine. Preferred bases are potassium tert-butoxide, sodium methoxide and sodium hydride.

Reaction solvents suitable for use in the present invention include organic solvents such as ether, tetrahydrofuran, ethylene glycol dimethyl ether, toluene and mixtures thereof. Preferred reaction solvents are tetrahydrofuran and ethylene glycol dimethyl ether.

Starting formula II haloacetaldehyde di($C_1$-$C_4$ alkyl) acetal compounds are prepared according to the procedures of Beilsteins Handbuch Der Organischen Chemie, Band I, System-Number 1-151, pages 611, 624 and 625, 1918.

Molluscicidal 2,4,5-trihalopyrrole-3-carbonitrile compounds of formula IV may be prepared by halogenating formula I compounds using standard halogenating techniques. The reaction may be illustrated as follows:

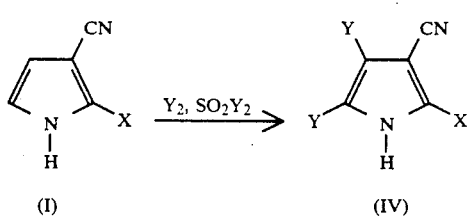

wherein X is Cl or Br and Y is Cl or Br.

Preparation of N-substituted formula IV 2,4,5-trihalopyrrole-3-carbonitriles may be achieved by reacting the formula IV pyrrole with an alkylating or acylating agent in the presence of an alkali metal alkoxide or hydride. The reactions are illustrated as follows:

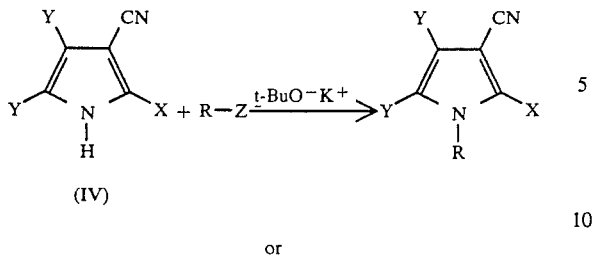

or

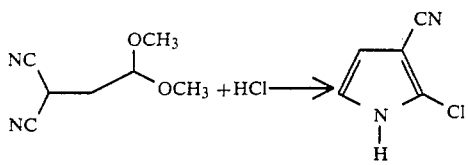

wherein

X is Cl or Br;
X is Cl or Br;
Z is halogen; and
R is $C_1$-$C_6$ alkyl optionally substituted with one to three halogen atoms, one cyano, one $C_1$-$C_4$ alkoxy, one $C_1$-$C_6$ alkylcarbonyloxy group, one $C_1$-$C_6$ alkoxycarbonyl group or one benzyloxy group.

In order to facilitate a further understanding of the invention, the following examples are presented to illustrate more specific details thereof. The invention is not to be limited thereby except as defined in the claims.

EXAMPLE 1

Preparation of (Formylmethyl)malononitrile dimethyl acetal

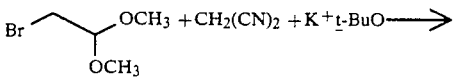

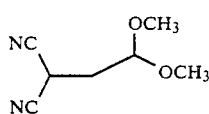

Malononitrile (20 g, 0.30 mol) is added to a 0° C. mixture of potassium tert-butoxide (37 g, 0.33 mol), ethylene glycol dimethyl ether (300 mL) and tetrahydrofuran (75 mL). After a short time, bromoacetaldehyde dimethyl acetal (52 g, 0.30 mol) is added to the reaction mixture. The reaction mixture is refluxed for 48 hours then cooled to room temperature. Solvent is removed and ether, water and brine are added to the reaction mixture. The organic layer is separated, dried over magnesium sulfate and concentrated in vacuo to give a brown oil. Flash chromatography of the oil using silica gel and a 5:1 hexanes/ethyl acetate solution as eluant yields a colorless oil which is distilled to obtain the title compound as a colorless oil (10 g; 21%, bp 110°–115° C., 3 mmHg) which is identified by IR and NMR spectral analyses.

EXAMPLE 2

Preparation of 2-Chloropyrrole-3-carbonitrile

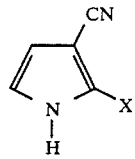

Hydrochloric acid (7 mL, 37%) is added to (formylmethyl)malononitrile dimethyl acetal (2 g, 0.013 mol). The reaction mixture exotherms slightly to 33°–37° C. where it stays for about 10 minutes. After another 20 minutes of stirring, a light colored solid precipitates. At this point, the reaction mixture is poured over an ice-water mixture and vacuum filtered. The resultant orange solid is dissolved in ethyl acetate and flash chromatographed using silica gel and 3:1 hexane/ethyl acetate as eluant to give the title compound as a white solid (0.7 g, 43%, mp 105°–106° C.) which is identified by IR and NMR spectral analyses.

EXAMPLE 3

Preparation of 2-Bromopyrrole-3-carbonitrile

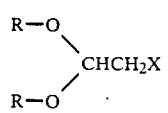

Hydrobromic acid (5 mL, 47–49%) is added to (formylmethyl)malononitrile dimethyl acetal (0.55 g, 0.0036 mol). After stirring for 30 minutes the reaction mixture is poured into an ice-water mixture and vacuum filtered. The solids are flash chromatographed using silica gel and 3:1 hexane/ethyl acetate as eluant to give the title compound as a beige solid (0.38 g, 62%, mp 102°–106° C.) which is identified by IR and NMR spectral analyses.

I claim:

1. A process for the preparation of a 2-halopyrrole-3-carbonitrile compound having the structural formula wherein X is Cl or Br which comprises reacting malononitrile with at least 1 molar equivalent of a base and at least 1 molar equivalent of a haloacetaldehyde di($C_1$-$C_4$ alkyl) acetal compound having the structural formula wherein R is $C_1$-$C_4$ alkyl and X is as described above in the presence of a solvent to obtain a (formylmethyl)- malononitrile di($C_1$-$C_4$ alkyl) acetal compound having the structure

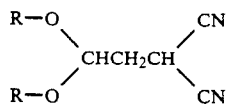

wherein R is as described above and reacting said (formylmethyl)malononitrile di($C_1$-$C_4$ alkyl) acetal compound with at least 1 molar equivalent of a hydrogen halide acid to form said 2-halopyrrole-3-carbonitrile compound.

2. The process according to claim 1 wherein the base is present in the amount of about 1 to 3 molar equivalents and the haloacetaldehyde di($C_1$-$C_4$ alkyl) acetal is present in the amount of about 1 to 3 molar equivalents.

3. The process according to claim 1 wherein the hydrogen halide acid is hydrochloric acid or hydrobromic acid.

4. The process according to claim 1 wherein the base is selected from the group consisting of an alkali metal $C_1$-$C_6$ alkoxide, an alkali metal hydride and an alkali metal carbonate, and the solvent is selected from the group consisting of tetrahydrofuran, ether and ethylene glycol dimethyl ether.

* * * * *